United States Patent [19]
Takagi et al.

[11] Patent Number: 6,164,778
[45] Date of Patent: Dec. 26, 2000

[54] CORNEAL ENDOTHELIAL CELL PHOTOGRAPHING APPARATUS

[75] Inventors: Akinari Takagi; Kouji Nishio, both of Tokyo, Japan

[73] Assignee: Kabushiki Kaisha Topcon, Tokyo, Japan

[21] Appl. No.: 09/468,950

[22] Filed: Dec. 22, 1999

[30] Foreign Application Priority Data

Dec. 24, 1998 [JP] Japan .................................. 10-366305

[51] Int. Cl.$^7$ ...................................................... A61B 3/14
[52] U.S. Cl. ............................................................ 351/206
[58] Field of Search ..................................... 351/205, 206, 351/207, 208, 210, 214, 221; 600/587

[56] References Cited

U.S. PATENT DOCUMENTS

| | | | |
|---|---|---|---|
| 4,396,260 | 8/1983 | Takizawa et al. | 351/206 |
| 4,597,650 | 7/1986 | Yoshino et al. | 351/214 |
| 5,250,965 | 10/1993 | Abe et al. | 351/221 |

FOREIGN PATENT DOCUMENTS 5-146410  6/1993  Japan .
8-117190  5/1996  Japan .

Primary Examiner—George Manuel
Attorney, Agent, or Firm—Oblon, Spivak, McClelland, Maier & Neustadt, P.C.

[57] ABSTRACT

A corneal endothelial cell photographing apparatus comprises a first slit plate provided with a slit, a photographing light projecting optical system for obliquely projecting photographing light for photographing a corneal endothelial cell of an eye to be tested through the slit of the first slit plate on the eye, an observation light projecting optical system for projecting observation light through the slit of the first slit plate on the eye for observation prior to photographing the corneal endothelial cell of the eye, an observing and photographing optical system for guiding the observation light reflected from the cornea of the eye and the photographing light reflected from the cornea of the eye to an image pickup device for the observation and photographing of the corneal endothelial cell of the eye, a second slit plate provided with a slit narrower than that of the first slit plate, and a Z-alignment measuring light projecting optical system for projecting alignment measuring light through the slit of the second slit plate on the eye to measure the position of a main unit of the corneal endothelial cell photographing apparatus relative to the eye with respect to directions along the optical axis of the eye.

7 Claims, 6 Drawing Sheets

CORNEAL ENDOTHELIAL CELL PHOTOGRAPHING APPARATUS

BACKGROUND OF THE INVENTION

1. Field of the Invention

The present invention relates to a corneal endothelial cell photographing apparatus for photographing endothelial cells of a cornea.

2. Description of the Related Art

A corneal endothelial cell photographing apparatus disclosed in Japanese Patent Laid-open No. Hei 5-146410 projects a slit light beam obliquely on an eye to be tested, and receives the slit light beam reflected from the cornea by an image pickup device, such as a CCD camera to form an image of corneal endothelial cells.

This prior art corneal endothelial cell photographing apparatus has a photographing light projecting optical system that projects a photographing light beam obliquely on the eye to form an image of corneal endothelial cells of the eye. The photographing light projecting optical system is used also as an observation light projecting optical system for projecting an observation light beam obliquely on the eye to observe the corneal endothelial cells prior to photographing and a Z-alignment measuring light projecting optical system for projecting an alignment measuring light beam on the eye to measure the position of a main unit of the corneal endothelial cell photographing apparatus relative to the eye with respect to a Z-direction (forward-backward direction). The photographing light projecting optical system is provided with a slit plate to project a slit light beam.

The corneal endothelial cell photographing apparatus disclosed in Japanese Patent Laid-open No. Hei 5-146410 uses a single slit plate for projecting the photographing light beam, the observation light beam and the alignment measuring light beam. The photographing light beam, the observation light beam and the alignment measuring light beam passed through the slit of the slit plate are slit light beam of the same width. When the single slit plate is thus used for projecting the photographing light beam, the observation light beam and the alignment measuring light beam, it is impossible to achieve both photographing a wide area and an accurate alignment measurement.

If the width of the slit of the slit plate is reduced to increase the accuracy of the alignment measurement, the width of the photographing slit light beam is reduced accordingly and the narrow photographing slit light beam is able to illuminate only a limited photographing area. If the width of the slit of the slit plate is increased to illuminate an enlarged photographing area, the accuracy of the alignment measurement decreases.

A corneal endothelial cell photographing apparatus disclosed in Japanese Patent Laid-open No. Hei 8-117190 employs two slit plates, i.e., an observation slit plate provided with a narrow slit and a photographing slit plate provided with a wide slit, and uses the photographing slit plate in combination with a photographing light projecting optical system and the observation slit plate in combination with an observation light projecting optical system and a Z-alignment measuring optical system. Thus, a wide area can be photographed and Z-alignment measuring accuracy can be improved.

However, the corneal endothelial cell photographing apparatus disclosed in Japanese Patent Laid-open No. Hei 8-117190 has the disadvantage that only a narrow area of the corneal endothelium can be observed when observing corneal endothelial cells prior to photographing.

The corneal endothelial cell photographing apparatus disclosed in Japanese Patent Laid-open No. Hei 8-117190 uses the same slit plate by both the observation light projecting optical system and the Z-alignment measuring light projecting optical system, and the slit plate is provided with the narrow slit in view of achieving the accurate alignment measurement. Therefore, although an image of a wide area can be photographed as typically illustrated in FIG. 8, only a narrow area of a width smaller than that of an image formed by photographing can be observed. Indicated at S1 in FIG. 8 is a photographed image of corneal endothelial cells, and indicated at S2 in FIG. 9 is an observed image of corneal endothelial cells.

SUMMARY OF THE INVENTION

It is an object of the present invention to provide a corneal endothelial cell photographing apparatus permitting the observation of a wide area in a corneal endothelial cell without decreasing the accuracy of alignment measurement, and capable of photographing a wide area in the corneal endothelial cell.

According to a first aspect of the present invention, a corneal endothelial cell photographing apparatus comprises: a first slit plate provided with a slit; a photographing light projecting optical system for obliquely projecting photographing light for photographing a corneal endothelial cell of an eye to be tested through the slit of the first slit plate on the eye; an observation light projecting optical system for projecting observation light through the slit of the first slit plate on the eye for observation prior to photographing the corneal endothelial cell of the eye; an observing and photographing optical system for guiding the observation light reflected from the cornea of the eye and the photographing light reflected from the cornea of the eye to an image pickup device to enable the observation and photographing of the corneal endothelial cell of the eye; a second slit plate provided with a slit narrower than that of the first slit plate; and a Z-alignment measuring light projecting optical system for projecting alignment measuring light through the slit of the second slit plate on the eye to measure the position of a main unit of the corneal endothelial cell photographing apparatus relative to the eye with respect to directions along the optical axis of the eye.

The light beams of light projected by the photographing light projecting optical system and the observation light projecting optical system are formed in wide slit light beams by the first slit plate. The beam of light projected by the Z-alignment measuring light projecting optical system is formed in a narrow slit light beam by the second slit plate. Therefore, corneal endothelial cells in a wide area can be observed and can be photographed without decreasing the accuracy of alignment measurement.

According to a second aspect of the present invention, the corneal endothelial cell photographing apparatus uses visible light as the photographing light and uses infrared rays as the observation light and the alignment measuring light.

Thus, the examiner's sensation of dazzling light during the alignment measurement and observation prior to the photographing can be alleviated.

According to a third aspect of the present invention, the corneal endothelial cell photographing apparatus uses light in a first infrared region as observation light, and light in a second infrared region having a wavelength different from that of the light in the first infrared region as alignment measuring light.

Thus, loss in the optical systems can be reduced, and the respective light quantities of light projected by the optical systems can be reduced. Consequently, load on the examiner and power consumption can be reduced.

According to a fourth aspect of the present invention, a corneal endothelial cell photographing apparatus comprises: a first light source that emits photographing light for illuminating a corneal endothelial cell of an eye to be tested for photographing; a second light source that emits observation light for illuminating the corneal endothelial cell of the eye for observation prior to the photographing; a third light source that emits alignment measuring light for measuring the position of a main unit the corneal endothelial cell photographing apparatus relative to the eye with respect directions along the optical axis of the eye; a first slit plate provided with a slit; a photographing light projecting optical system for obliquely projecting the photographing light through the slit of the first slit plate toward the eye; a first light splitting member disposed between the first light source and the first slit plate; an observation light projecting optical system for projecting the observation light through the first light splitting member and the slit of the first slit plate toward the eye; an observing and photographing optical system for guiding the photographing light reflected from the cornea of the eye and the observation light reflected from the cornea of the eye to an image pickup device for the observation and the photographing of the corneal endothelial cell of the eye; a second light splitting member disposed between the first slit plate and the eye; a second slit plate provided with a slit narrower than that of the first slit plate; and a Z-alignment measuring light projecting optical system for projecting the alignment measuring light through the slit of the second slit plate and the second light splitting member toward the eye.

Light beams projected by photographing light projecting optical system and the observation light projecting optical system travel through the first light splitting member to the first slit plate and are shaped in wide slit light beams. A light beam projected by the Z-alignment measuring light projecting optical system is shaped in a narrow slit light beam by the second slit plate. Thus, corneal endothelial cells in a wide area can be observed and can be photographed without decreasing the accuracy of alignment measurement.

According to a fifth aspect of the present invention, the first light splitting member is a first dichroic mirror that transmits visible light and reflects light in the first infrared region, and the second,light splitting member is a second dichroic mirror that transmits visible light and light in the first infrared region and reflects light in the second infrared region.

BRIEF DESCRIPTION OF THE DRAWINGS

The above and other objects, features and advantages of the present invention will become more apparent from the following description taken in connection with the accompanying drawings, in which.

DESCRIPTION OF THE PREFERRED EMBODIMENTS

A corneal endothelial cell photographing apparatus S in a preferred embodiment according to the present invention will be described with reference to the accompanying drawings.

Figure 1:
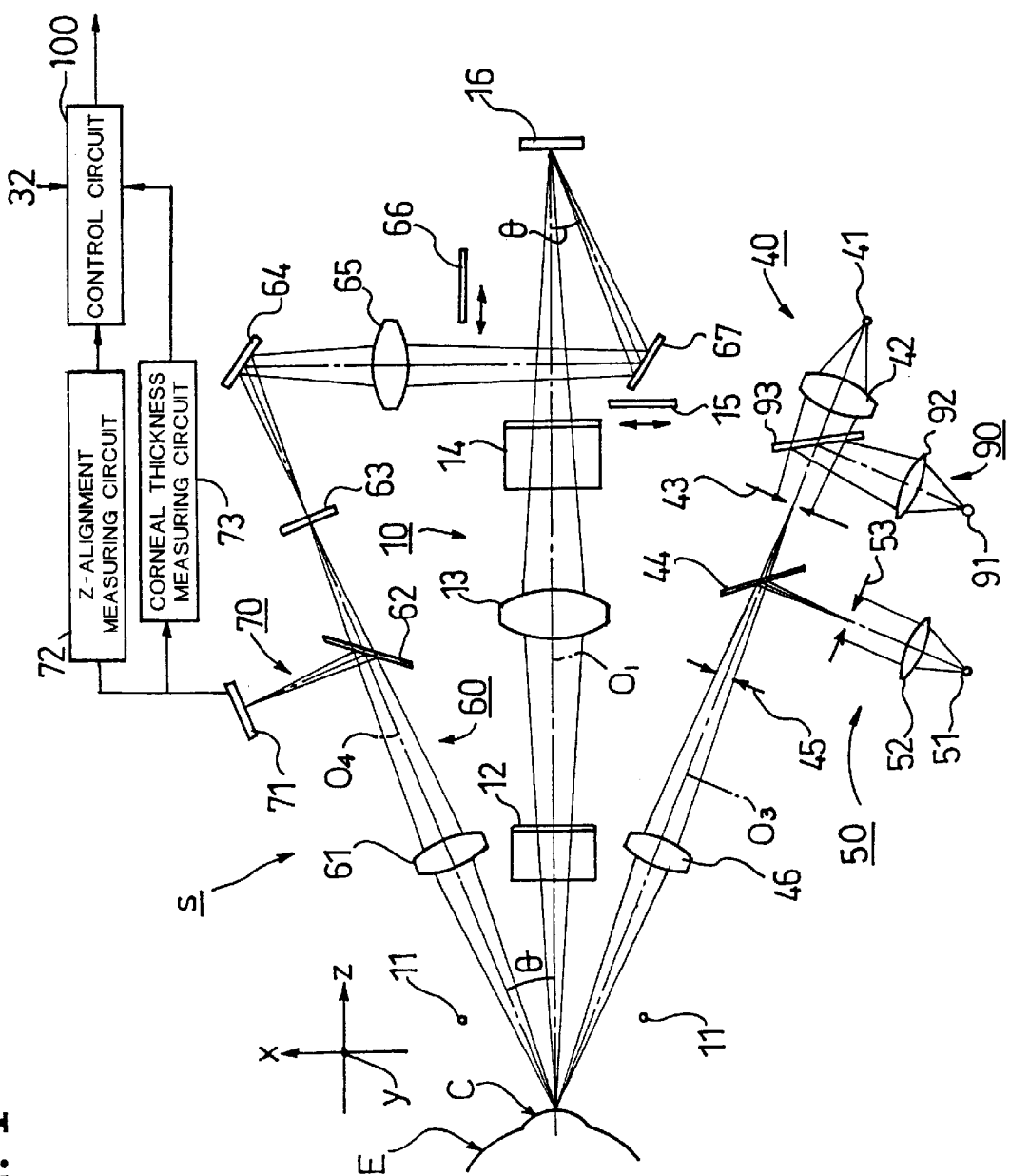
FIG. 1 is a diagrammatic plan view of principal optical systems of a corneal endothelial cell photographing apparatus in a preferred embodiment according to the present invention.
Figure 2:
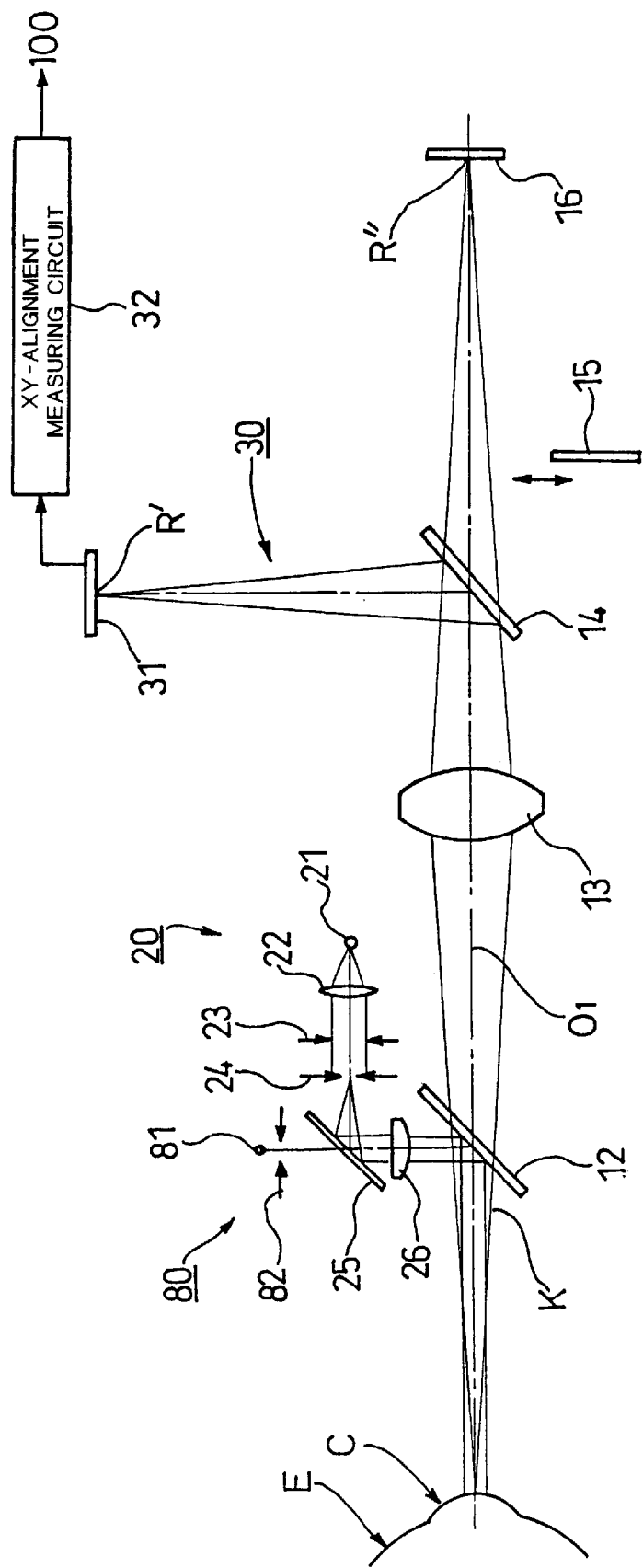
FIG. 2 is a diagrammatic side view of an XY-alignment index light projecting optical system, an XY-alignment measuring optical system and a fixation point projecting optical system included in the corneal endothelial cell photographing apparatus shown in FIG. 1.

Referring to FIGS. 1 and 2 showing optical systems included in the corneal endothelial cell photographing apparatus S, the corneal endothelial cell photographing apparatus S comprises an anterior segment observing optical system 10, an XY-alignment index light projecting optical system 20, an XY-alignment measuring optical system 30, a photographing light projecting optical system 40, a Z-alignment measuring light projecting optical system 50, an observation light projecting optical system 90, an observing and photographing optical system 60, a Z-alignment measuring optical system 70 and a fixation target projecting optical system 80.

The anterior segment observing optical system 10 for observing the anterior segment of an eye E to be tested comprises an infrared light source 11 for illuminating the anterior segment, a semitransparent mirror 12, an objective 13, a semitransparent mirror 14, a shading plate 15 and a CCD camera 16. Indicated at $O_1$ is the optical axis of the anterior segment observing optical system 10.

Light emitted by the infrared light source 11 to illuminate the anterior segment of the eye E and reflected by the anterior segment of the eye E travels through the semitransparent mirror 12, the objective 13 and the semitransparent mirror 14, falls on the CCD camera 16 and forms an image of the anterior segment of the eye E on the CCD camera 16. The shading plate 15 is moved away from the optical path when observing the anterior segment and is disposed on the optical path when observing corneal endothelial cells and when photographing corneal endothelial cells.

The XY-alignment index light projecting optical system 20 projects an XY-alignment index light beam on the cornea C of the eye E for the measurement of the position of the corneal endothelial cell photographing apparatus S relative to the cornea C of the eye E with respect to directions along the X-axis (horizontal directions in FIG. 2) and directions along the Y-axis (vertical directions in FIG. 2). The XY-alignment index light projecting optical system 20 comprises an infrared light source 21, a condenser lens 22, an aperture stop 23, a pinhole plate 24 for forming an index, a dichroic mirror 25, a projection lens 26 and the semitransparent mirror 12.

The projection lens 26 is disposed on the optical path with its focal point coincided with the pinhole plate 24. Infrared rays emitted by the infrared light source 21 are gathered by the condenser lens 22 and travel through the aperture stop 23 to the pinhole plate 24. The infrared rays which passes through the pinhole of the pinhole plate 24 is reflected by the dichroic mirror 25 and are collimated by the projection lens 26 to form an index light beam K. The index light beam K is reflected by the semitransparent mirror 12 toward the cornea C.

Figure 3:
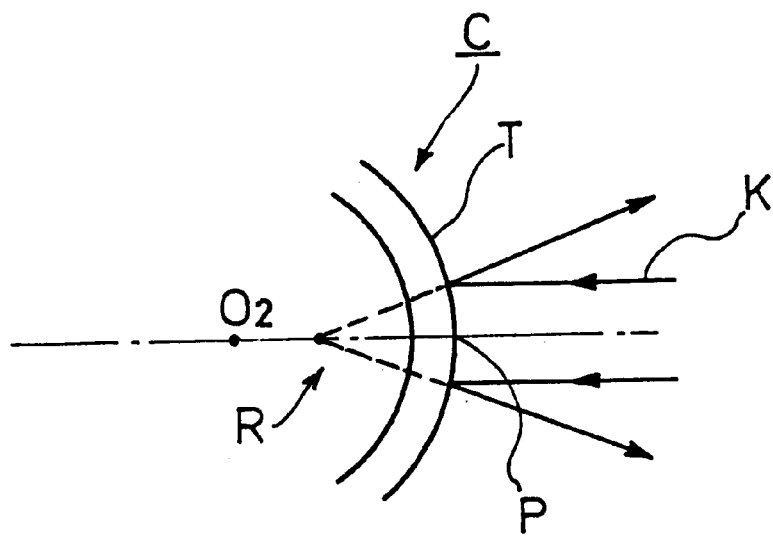
FIG. 3 is a diagrammatic view of assistance in explaining a mode of reflection of index light rays by a cornea.

The index light beam K projected on the cornea C is reflected by the corneal surface T, i.e., the surface of the cornea C, so that a bright point R is formed at the middle between the vertex P of the cornea C and the center $O_2$ of curvature of the cornea C as shown in FIG. 3. The aperture stop 23 is disposed such that the aperture stop 23 and the vertex P of the cornea C are conjugate with respect to the projection lens 26.

The XY-alignment measuring optical system 30 receives the index light beam K reflected from the cornea C and determines the position of the corneal endothelial cell photographing apparatus S in an XY plane defined by the X-axis and the Y-axis relative to the cornea C. The XY-alignment measuring optical system 30 comprises the semitransparent mirror 12, the objective 13, the semitransparent mirror 14 and a photosensor 31.

The index light beam K projected by the index light projecting optical system 20 on the cornea C and reflected by the cornea C so as to form the bright point R travels through the semitransparent mirror 12, is converged so as to be focused on the photosensor 31 by the objective 13, and part of the reflected index light beam K is reflected by the semitransparent mirror 14 so as to form an image R' of the bright point R on the photosensor 31. The photosensor 31 is a photodetection device capable of position indication, such as a PSD.

An XY-alignment measuring circuit 32 calculates the position of the corneal endothelial cell photographing apparatus S relative to the cornea C with respect to directions along the X-axis and the Y-axis on the basis of the output of the photosensor 31, and gives calculated data to a control circuit 100.

Figure 4:
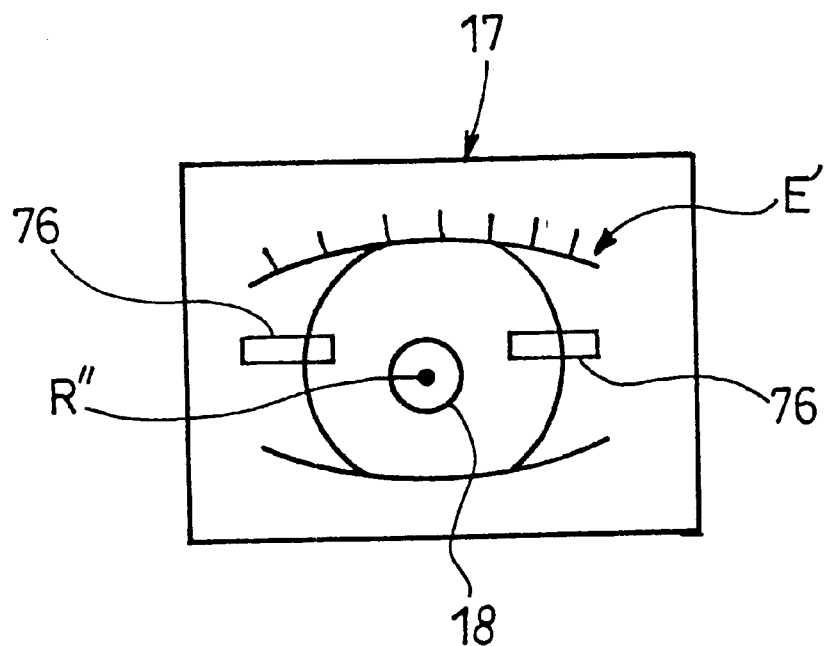
FIG. 4 is a front view of a screen of a monitor device included in the corneal endothelial cell photographing apparatus shown in FIG. 1 displaying an image of the anterior segment of the eye.

The index light beam K which is reflected from the cornea C and traveled through the semitransparent mirror 14 forms a bright point image R", i.e., an image of the bright point R, on the CCD camera 16. Then the CCD camera 16 gives an image signal to a monitor device, not shown. The monitor device displays on its screen 17 an anterior segment image E', i.e., an image of the anterior segment of the eye E and the bright point image R" as shown in FIG. 4. Indicated at 18 in FIG. 4 is a mark produced by a picture producing means, not shown, and indicating an allowable range of alignment. Observing the screen 17, the examiner moves the corneal endothelial cell photographing apparatus S relative to the eye E to locate the bright point image R" inside the mark 18 and to focus the corneal endothelial cell photographing apparatus S on the cornea C for XY-alignment.

The photographing light projecting optical system 40 projects a photographing slit light beam for photographing corneal endothelial cells obliquely on the cornea C. The photographing light projecting optical system 40 comprises a xenon lamp (first light source) 41, i.e., a photographing light source, a condenser lens 42, a dichroic mirror (first light splitting member) 93, a slit plate (first slit plate) 43, a dichroic mirror (second light splitting member) 44, an aperture stop 45 and an objective 46. Indicated at $O_3$ in FIG. 1 is the optical axis of the photographing light projecting optical system 40. The photographing light source 41 emits visible light of wavelengths in the range of 400 to 700 nm. The dichroic mirror 93 transmits light of wavelengths not greater than 735 nm and intercepts light of wavelengths exceeding 735 nm, which will be described later.

The slit plate 43 is provided with a slit of a width that enables to photograph a wide area in the corneal endothelium and prevents the deterioration of picture quality attributable to the inclusion of reflected light from the ectocornea. The dichroic mirror 44 transmits light of wavelengths not greater than 820 nm and intercepts light of wavelengths exceeding 820 nm, which will be described later.

Visible light rays emitted by the photographing light source 41 is gathered by the condenser lens 42, pass through the dichroic mirror 93, the slit plate 43, the dichroic mirror 44 and the aperture stop 45, and are focused on the cornea C by the objective 46 to illuminate an area in the cornea C extending across the cornea C.

Figure 5A:
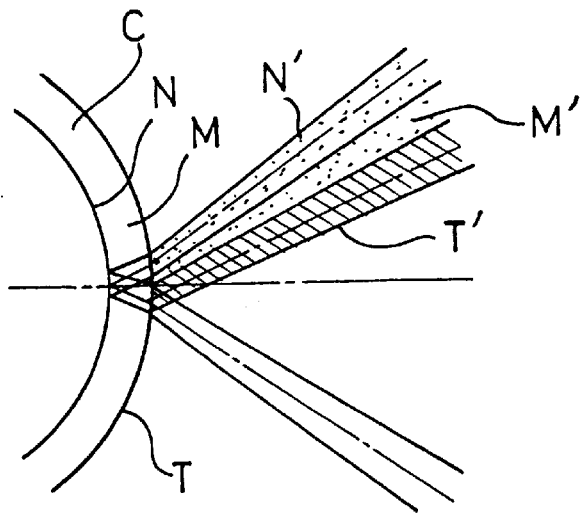
FIG. 5(a) is a diagrammatic view of assistance in explaining a mode of reflection of a slit light beam by the cornea.

FIG. 5(a) illustrates a mode of reflection of the slit light beam projected by the photographing light projecting optical system 40 on the cornea C, by the cornea C. Part of the slit light beam is reflected in a reflected light beam T' by the ectocornea T, i.e., the boundary between the cornea C and the atmosphere, and part of the slit light beam penetrated the ectocornea T is reflected in a reflected light beam N' by a corneal endothelial surface N. The light quantity of the reflected light beam T' from the ectocornea T is the highest, the light quantity of the reflected light beam N' from the corneal endothelial surface N is lower than that of the reflected light beam T', and the light quantity of reflected light beam M' reflected from the corneal stroma M is the lowest.

The observation light projecting optical system 90 projects an observation slit light beam for the observation of corneal endothelial cells obliquely on the cornea C. The observation light projecting optical system 90 comprises an observation light source (second light source) 91 that emits near-infrared rays of about 770 nm in wavelength, i.e., light rays in a first infrared region, a condenser lens 92, a dichroic mirror 93, the slit plate 43, the dichroic mirror 44, the aperture stop 45 and the objective 46. The infrared rays emitted by the observation light source 91 are gathered by the condenser lens 92, are reflected by the dichroic mirror 93 and travel through the slit of the slit plate 43 in an observation slit beam.

Then, the observation slit beam travels through the dichroic mirror 44 and the aperture stop 45, the observation slit beam is focused by the objective 46 on the cornea C. The observation slit light beam, similar to the photographing slit beam projected by the photographing light projecting optical system 40, is reflected as shown in FIG. 5(a).

The Z-alignment measuring light projecting optical system 50 projects obliquely on the cornea C a Z-alignment measuring slit light beam for measuring the position of the corneal endothelial cell photographing apparatus S relative to the cornea C with respect to directions along the Z-axis. The Z-alignment measuring light projecting optical system 50 comprises a Z-alignment measuring light source (third light source) 51 that emits infrared rays of about 870 nm in wavelength, a condenser lens 52, a slit plate (second slit plate) 53, the dichroic mirror 44, the aperture stop 45 and the objective 46. The Z-alignment measuring light source 51 emits light rays of a wavelength in a second infrared region. The wavelength of the light rays emitted by the Z-alignment measuring light source 51 is different from that of the light rays emitted by the observation light source 91. A slit narrower than that of the slit plate 43 is formed in the slit plate 53 for the accurate Z-alignment measurement.

The infrared rays emitted by the Z-alignment measuring light source 51 are gathered by the condenser lens 52 and are shaped in a Z-alignment measuring slit beam by the slit plate 53. The Z-alignment measuring slit beam is reflected by the dichroic mirror 44, travels through the aperture stop 45 and is focused on the cornea C by the objective 46. The Z-alignment measuring slit beam projected by the Z-alignment measuring light projecting optical system 50, similar to the photographing slit beam projected by the photographing light projecting optical system 40, is reflected as shown in FIG. 5(a).

Figure 7A:
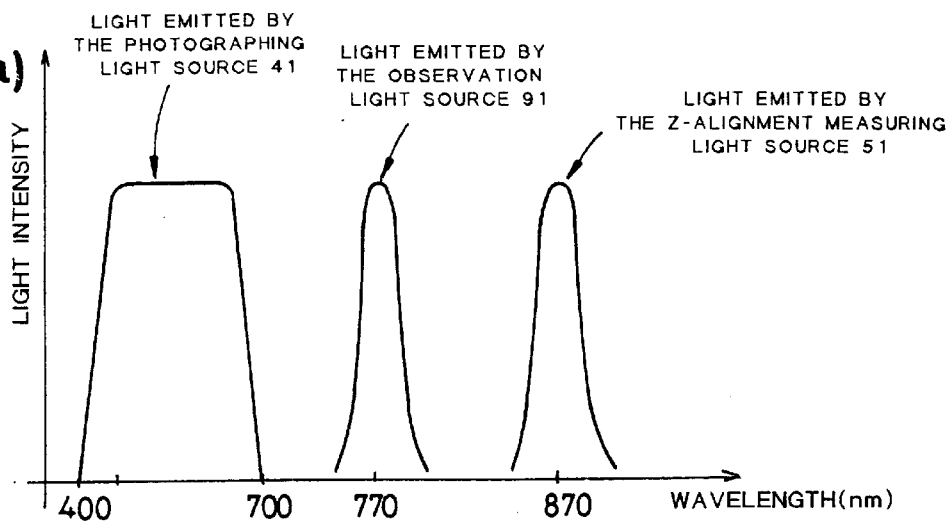
FIG. 7(a) is a graph showing the respective wavelengths of light rays emitted by three light sources 41, 91 an 51 included in the corneal endothelial cell photographing apparatus shown in FIG. 1.
Figure 7B:
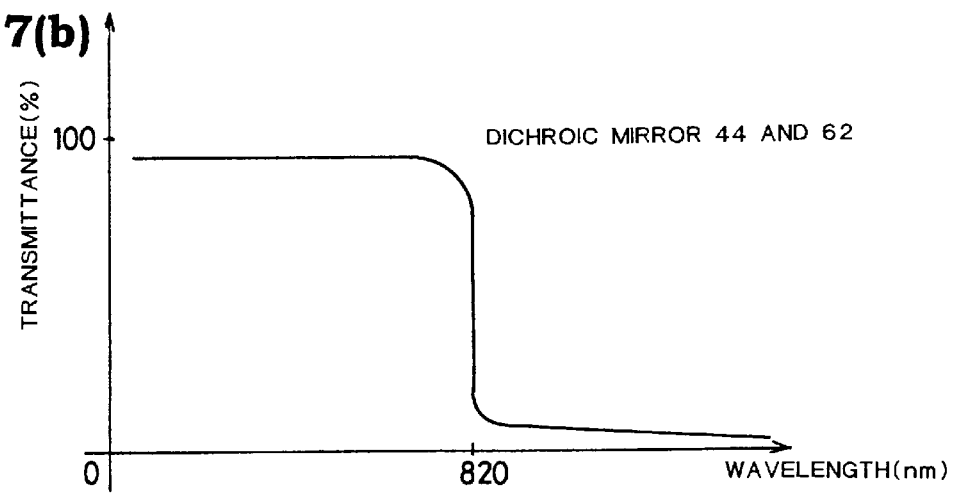
FIG. 7(b) is a graph showing the light transmittance characteristics of dichroic mirrors 44 and 62 included in the corneal endothelial cell photographing apparatus shown in FIG. 1.
Figure 7C:
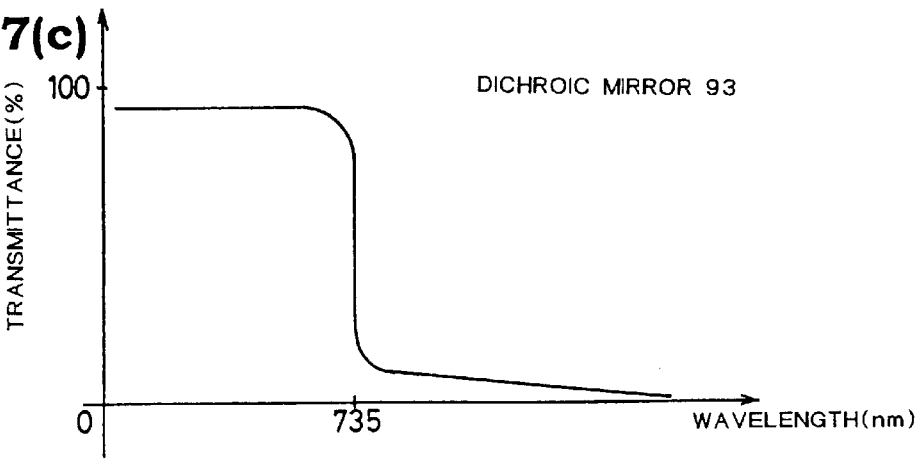
FIG. 7(c) is a graph showing the light transmittance characteristic of a dichroic mirror 93 included in the corneal endothelial cell photographing apparatus shown in FIG. 1.
Figure 8:
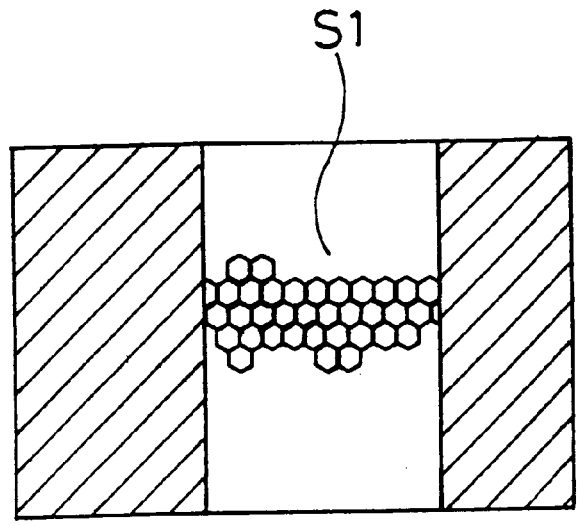
FIG. 8 is a diagrammatic view of an image of corneal endothelial cells in a wide area in a corneal endothelium formed by a conventional corneal endothelial cell photographing apparatus.
Figure 9:
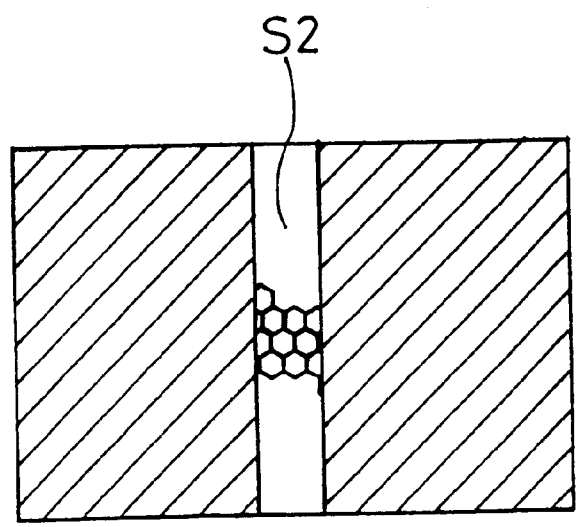
FIG. 9 is a diagrammatic view of an image of corneal endothelial cells observed by the conventional corneal endothelial cell photographing apparatus used for forming the image shown in FIG. 8.

The respective wavelengths of the light rays respectively emitted by the photographing light source 41, the observation light source 91 and the Z-alignment measuring light source 51 are different from each other. For example, the wavelengths of the light rays respectively emitted by the photographing light source 41, the observation light source 91 and the Z-alignment measuring light source 51 are 400 to 700 nm, 770 nm and 870 nm, respectively, as shown in FIG. 7(a). The transmittances of the dichroic mirrors 44 and 62 are substantially 100% to light rays of wavelengths less than 820 nm, and decrease sharply with the increase of wavelength beyond 820 nm to values nearly equal to 0% as shown in FIG. 7(b). The transmittance of the dichroic mirrors 93 is substantially 100% to light rays of wavelengths less than 735 nm, and decreases sharply with the increase of wavelength beyond 735 nm to values nearly equal to 0% as shown in FIG. 7(c).

The observing and photographing optical system 60 and the photographing light projecting optical system 40 are symmetrically provided with respect to the optical axis $O_1$ of the anterior segment observing optical system 10. The observing and photographing optical system 60 comprises an objective 61, the dichroic mirror 62, a mask 63, a mirror 64, a relay lens 65, a shading plate 66, a mirror 67 and the CCD camera 16. Indicated at 04 in FIG. 1 is the optical axis of the observing and photographing optical system 60. The dichroic mirror 62 transmits light rays of wavelengths not greater than 820 nm and intercepts light rays of wavelengths exceeding 820 nm. The mask 63 intercepts reflected light rays other than those forming an image of corneal endothelial cells. The mirror 67 is disposed outside an optical path for the anterior segment observing light rays and is inclined with respect to $O_1$ at an angle θ equal to the inclination angle of the eye E with respect to $O_4$.

Figure 5B:
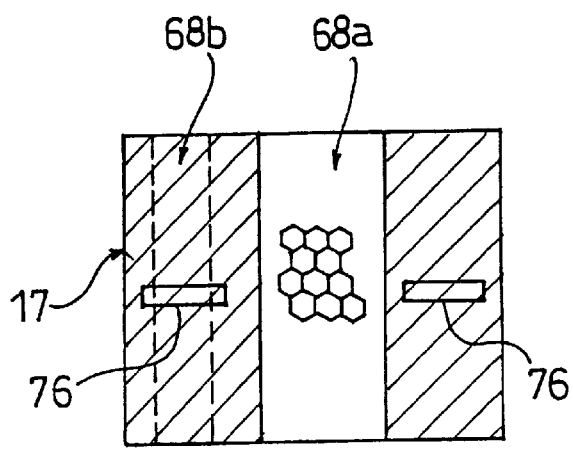
FIG. 5(b) is a front view of a screen of a monitor device displaying an image of corneal endothelial cells.

The slit beams of light rays projected by the photographing light projecting optical system 40 and the observation light projecting optical system 90 and reflected from the cornea C are converged by the objective 61, travels through the dichroic mirror 62 and form an image of corneal endot-helium cells on the mask 63. Light rays other than those forming the image of corneal endothelium cells are intercepted by the mask 63. The light rays from the mask 63 are reflected by the mirror 64, are converged by the relay lens 65, are reflected by the mirror 67 and form an image of corneal endothelium cells on the CCD camera 16. The CCD camera 16 gives an image signal representing the image formed thereon to the monitor device. Then, the monitor device displays an image 68a of corneal endothelium cells as shown in FIG. 5(b) on its screen 17. In FIG. 5(b), a section 68b demarcated by broken lines represents an optical image that may be formed by the reflected light beam T' from the corneal surface T if the reflected light beam T' is not intercepted by the mask 63. When observing or photographing corneal endothelium cells, the shading plate 66 is retracted from the optical path and is located on the optical path when observing the anterior segment.

The fixation target projecting optical system 80 comprises a fixation target light source 81 that emits visible light, a pinhole plate 82, the dichroic mirror 25, the projection lens 26 and the semitransparent mirror 12. Fixation target light emitted by the fixation target light source 81 travels through the pinhole plate 82 and the dichroic mirror 25, is collimated in a light beam by the projection lens 26, and the light beam is reflected by the semitransparent mirror 12. The subject is required to gaze at the fixation target to fix the subject's visual line.

Figure 6A:
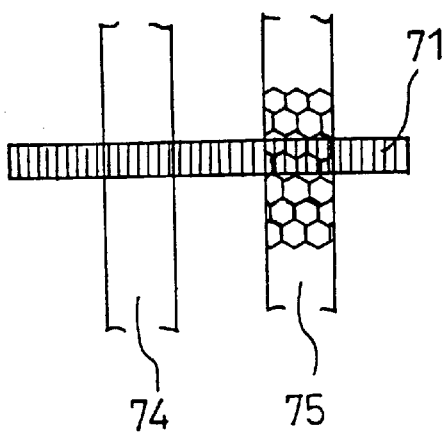
FIG. 6(a) is a diagrammatic view of assistance in explaining the relation between a linear photosensor included in the corneal endothelial cell photographing apparatus shown in FIG. 1 and images of corneal endothelial cells.
Figure 6B:
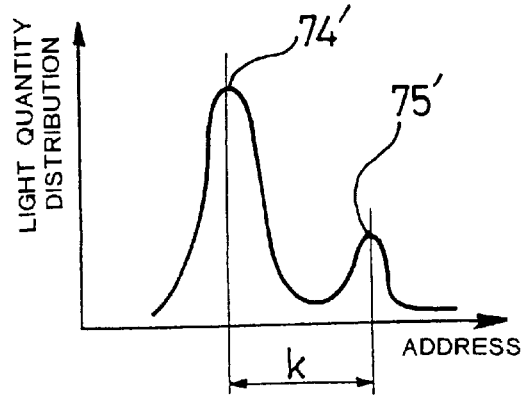
FIG. 6(b) is a graph of assistance in explaining the relation between the light quantity distribution of reflected light beam on the linear photosensor and alignment measurement.

The Z-alignment measuring optical system 70 comprises the objective 61, the dichroic mirror 62 and a focus detecting sensor 71. The slit light beam projected by the Z-alignment measuring light projecting optical system 50 and reflected from the cornea C is converged by the objective 61, is reflected by the dichroic mirror 62 and is focused on the focus detecting sensor 71 in an image. The focus detecting sensor 71 is a photosensor capable of determining a light quantity distribution, such as a linear photosensor. An image as shown in FIG. 6(a) is formed on the focus detecting sensor 71. The focus detecting sensor 71 provides an image signal representing a light quantity distribution as shown in FIG. 6(b). In FIG. 6(a), a section 74 is an image of the reflected light beam T' from the ectocornea T, and a section 75 is an image of the reflected light beam N' from the corneal endothelial surface N. A Z-alignment measuring circuit 72 detects a peak 75' in the light quantity distribution curve of the reflected light beam N' shown in FIG. 6(b) on the basis of the output of the focus detecting sensor 71 to determine the position of the corneal endothelial surface and gives a signal representing the position of the corneal endothelial surface to the control circuit 100. A corneal thickness measuring circuit 73 determines the interval K (FIG. 6(b)) between the peak 74' of the distribution curve of the reflected light beam T' and the peak 75' of the distribution curve of the reflected light beam N' on the basis of the output of the focus detecting sensor 71, calculates the thickness of the cornea C on the basis of the interval K, and gives the calculated thickness of the cornea C to the control circuit 100.

The control circuit 100 notifies the examiner of information about Z-alignment on the basis of the output of the Z-alignment measuring circuit 72 by the length of alignment indicating bars 76 shown in FIGS. 4 and 5(b).

Procedures for measurement and photographing will be described hereinafter. The control circuit 100 turns on the light sources 11, 21, 51 and 81. The examiner aligns the corneal endothelial cell photographing apparatus S roughly with the eye E, observing the picture of the anterior segment of the eye E displayed on the screen of the monitor device. Upon the confirmation of completion of the alignment of the corneal endothelial cell photographing apparatus S with the eye E from the outputs of the XY-alignment measuring circuit 32 and the Z-alignment measuring circuit 72, the control circuit 100 turns on the observation light source 91, disposes the shading plate 15 on the optical path and moves the shading plate 66 away from the optical path. Consequently, an image of the anterior segment displayed on the screen 17 of the monitor device is changed for an image of corneal endothelial cells.

Observing the image of the corneal endothelial cells, the examiner continues operations for aligning the corneal endothelial cell photographing apparatus S with the eye E. The width of an image of corneal endothelial cells displayed on the screen 17 is equal to that of a photograph of corneal endothelial cells. Thus, the examiner is able to observe a wide area in the corneal endothelium before photographing.

Upon the determination of the completion of the alignment of the corneal endothelial cell photographing apparatus S with the eye E with respect to directions along the X-axis and the Y-axis, and the completion of focusing of the observing and photographing optical system 60 on the surface of the corneal endothelium by the XY-alignment measuring circuit 32 and the Z-alignment measuring circuit 72, the corneal thickness measuring circuit 73 calculates the thickness of the cornea C on the basis of the output of the focus detecting sensor 71 and gives calculated data to the control circuit 100. The photographing light source 41 is driven for light emission to photograph corneal endothelial cells. The thickness of the cornea C and an image of the corneal endothelial cells are displayed on the screen 17 of the monitor device.

Although the single slit plate is used by both the photographing light projecting optical system and the observation light projecting optical system in the embodiment described above, the corneal endothelial cell photographing apparatus may be provided with slit plates respectively for the photographing light projecting optical system and the observation light projecting optical system.

Although the invention has been described in its preferred form with a certain degree of particularity, obviously many changes and variations are possible therein. It is therefore to be understood that the present invention may be practiced otherwise than as specifically described herein without departing from the scope and spirit thereof.

What is claimed is:

1. A corneal endothelial cell photographing apparatus comprising:

a first slit plate provided with a slit;

a photographing light projecting optical system for obliquely projecting photographing light for photographing a corneal endothelial cell of an eye to be tested through the slit of the first slit plate on the eye;

an observation light projecting optical system for projecting observation light through the slit of the first slit plate on the eye for observation prior to photographing the corneal endothelial cell of the eye;

an observing and photographing optical system for guiding the observation light reflected from the cornea of the eye and the photographing light reflected from the cornea of the eye to an image pickup device for the observation and photographing of the corneal endothelial cell of the eye;

a second slit plate provided with a slit narrower than that of the first slit plate; and a Z-alignment measuring light projecting optical system for projecting alignment measuring light through the slit of the second slit plate on the eye to measure the position of a main unit of the corneal endothelial cell photographing apparatus relative to the eye with respect to directions along the optical axis of the eye.

2. The corneal endothelial cell photographing apparatus according to claim 1, wherein the photographing light is visible light, and the observation light and the alignment measuring light are infrared rays.

3. The corneal endothelial cell photographing apparatus according to claim 2, wherein the observation light is light in a first infrared region, and the alignment measuring light is light in a second infrared region having a wavelength different from that of the light in the first infrared region.

4. A corneal endothelial cell photographing apparatus comprising:

a first light source that emits photographing light for illuminating a corneal endothelial cell of an eye to be tested for photographing;

a second light source that emits observation light for illuminating the corneal endothelial cell of the eye for observation prior to the photographing;

a third light source that emits alignment measuring light for measuring the position of a main unit of the corneal endothelial cell photographing apparatus relative to the eye with respect directions along the optical axis of the eye;

a first slit plate provided with a slit;

a photographing light projecting optical system for obliquely projecting the photographing light through the slit of the first slit plate toward the eye;

a first light splitting member disposed between the first light source and the first slit plate;

an observation light projecting optical system for projecting the observation light through the first light splitting member and the slit of the first slit plate toward the eye;

an observing and photographing optical system for guiding the photographing light reflected from the cornea of the eye and the observation light reflected from the cornea of the eye to an image pickup device for the observation and the photographing of the corneal endothelial cell of the eye;

a second light splitting member disposed between the first slit plate and the eye;

a second slit plate provided with a slit narrower than that of the first slit plate; and a Z-alignment measuring light projecting optical system for projecting the alignment measuring light through the slit of the second slit plate and the second light splitting member toward the eye.

5. The corneal endothelial cell photographing apparatus according to claim 4, wherein the photographing light is visible light, and the observation light and the alignment measuring light are infrared rays.

6. The corneal endothelial cell photographing apparatus according to claim 5, wherein the observation light is light in a first infrared region, and the alignment measuring light is light in a second infrared region having a wavelength different from that of the light in the first infrared region.

7. The corneal endothelial cell photographing apparatus according to claim 6, wherein the first light splitting member is a first dichroic mirror that transmits visible light and reflects light in the first infrared region, and the second light splitting member is a second dichroic mirror that transmits visible light and light in the first infrared region and reflects light in the second infrared region.

* * * * *